United States Patent
Patel et al.

(10) Patent No.: US 7,352,460 B2
(45) Date of Patent: Apr. 1, 2008

(54) DIRECTED COLOR STANDARD AND METHOD FOR USING SAME

(75) Inventors: Farhan Patel, Kowloon (HK); Amy Lee-Shank, Dublin, OH (US); Liss Sauer, Westerville, OH (US)

(73) Assignee: Mast Industries, Inc., Columbus, OH (US)

( * ) Notice: Subject to any disclaimer, the term of this patent is extended or adjusted under 35 U.S.C. 154(b) by 231 days.

(21) Appl. No.: 11/168,040

(22) Filed: Jun. 28, 2005

(65) Prior Publication Data

US 2006/0290927 A1 Dec. 28, 2006

(51) Int. Cl.
*G01J 3/42* (2006.01)
(52) U.S. Cl. ..................................... 356/319
(58) Field of Classification Search ............... 356/319, 356/402
See application file for complete search history.

(56) References Cited

U.S. PATENT DOCUMENTS

| | | | |
|---|---|---|---|
| 4,788,650 A | * | 11/1988 | Willis et al. ............... 356/405 |
| 4,954,976 A | * | 9/1990 | Noonan ....................... 703/6 |
| 2005/0117146 A1 | * | 6/2005 | Jung et al. .................. 356/402 |

\* cited by examiner

*Primary Examiner*—Kara E Geisel
(74) *Attorney, Agent, or Firm*—Ward & Olivo

(57) ABSTRACT

The present invention discloses a method for establishing a directed color standard. Color reflectance data is measured from a fabric to construct an initial color standard. Because all fabrics have inherent quality fluctuations, a second series of color reflectance measurements are taken at various locations on a fabric. The second series of color data is used to establish a narrower, directed color standard. The directed color standard can be used by an entity to more efficiently utilize a plurality of third party colored product providers because using the directed color standard results in fewer product rejections based on color deviation.

12 Claims, 6 Drawing Sheets

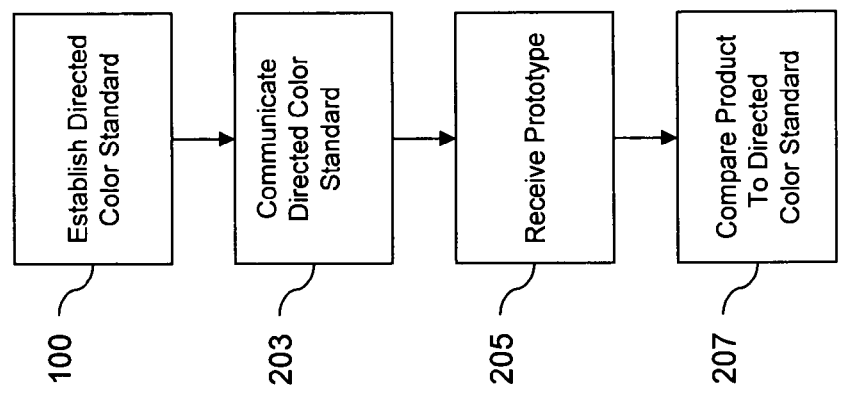

DIRECTED COLOR STANDARD AND METHOD FOR USING SAME

FIELD OF THE INVENTION

The invention relates to the field of color. Specifically, disclosed is a method for creating a directed color standard. Also disclosed is a method of using a directed color standard to more efficiently manage the color variability of a product.

BACKROUND OF THE INVENTION

Color can be defined as a quality of light with a particular wavelength. For instance, spectral color, or visible color, is an emission of light in the "rainbow" spectrum. Perceived color is the quality of light emission as conveyed by the human eye, combining the impressions of 3 types of light-sensitive cells within the eye.

Perceived color is the response to certain combinations of spectral colors by an individual. For instance, many people find that the color brown is visually appealing when combined with green and red. In addition, the color combination of blue, yellow and red is often pleasing. Product consumers typically purchase products that are appealing. As a result, consumers often purchase products that are visually appealing. Indeed, marketing firms and consumer product manufacturers employ "color consultants" to help boost sales by designing products with specific color combinations.

Color is particularly important in the world of fashion. Because there are a limited number of garment styles and cuts, garments can be differentiated by particular color combinations. As fashion trends change so do color combinations. In addition, perceived color is subjective, i.e., what one consumer finds appealing another may find unappealing. Consequently, there is constant consumer demand for garments with widely varying color combinations.

In addition, fashion, and textiles in particular, are particularly fractionated, global industries. There are countless dye houses, fabric providers, and garment producers. Each of these entities employs its own color development and/or management team. However, due to the subjective nature of color, standardization of a particular color scheme is problematic. As a result, producing textile garments can be a complicated process.

The first step in the production of a garment is its design. During this stage the designer chooses the type of fabric, the cut of the fabric, and its color. Next, the designer creates the garment. Typically, this involves ordering the fabric with its corresponding color from a vendor. Often, the designer solicits multiple vendors which may or may not have the fabric in the desired color. If it does not, the vendor must send the fabric to a dye house to be dyed. In either case, the color of the fabric must be matched to the designer's specifications. Often, each vendor is supplied with a color sample. After matching the color to the best of its ability, a vendor sends a sample of its product back to the designer for final approval.

As a result, a designer typically receives numerous fabric samples. Since there are inherent fluctuations in both the dye and the fabric used in production of the sample, a vendor usually obtains a plurality of fabrics with widely different color characteristics. This problem is compounded by the fact that perceived color is subjective. Further, color exhibits a phenomenon known as metamerism. Metamerism is the tendency of color to shift in hue as it is viewed under different lighting conditions and angles. As a result, color matching is often difficult. The deviation in color selection can have an adverse impact on retail sales. In addition, the above process can be very time consuming, resulting in a waste of valuable, limited resources.

To help alleviate this problem, designers have employed many well known color management techniques. The most obvious is visual inspection, in which a designer visually compares the sample received from a vendor to the designed color standard. However, this technique is flawed in that it relies on the subjective perception of the viewer. In addition, the problem of metamerism remains.

To alleviate the metameric effects of color, visual inspection can be standardized by viewing a sample at a constant angle under specific lighting conditions. A well known device which employs this technique is known as a "light box." However, like simple visual inspection, it relies on the subjective eye of the viewer.

To eliminate the problems associated with subjectivity, various color management systems now employ spectrophotometers. A spectrophotometer allows a viewer to objectively quantify physical characteristics of a color. Specifically, it measures the wavelength reflectance of a color. However, obtaining an exact reflectance match is next to impossible because of the inherent variability in both the dye formulas and the fabric. As a result, many designers that utilize a spectrophotometric color management process establish relative acceptable reflectance deviations.

The reflectance deviations can be determined by using commonly known statistical methods. Color management software has been developed which utilizes these well known methods. For instance, MATCHWIZARD™ PRO color matching software, available from Clariant Corporation of Charlotte, N.C., USA and ColorTools® software from DataColor Corporation of Lawrenceville, N.J., USA are well known in the art. These programs create batch distributions utilizing reflectance data. Specifically, these software programs plot contrast, brightness, and visible color difference data to create an acceptable color deviation from a standard midpoint. Colors are expressed as a number of positive or negative deviations from a midpoint. The positive and negative deviations are not assigned arbitrarily. Rather, positive deviations reflect deviations that are lighter, redder, more yellow, and brighter than the standard, while negative deviations indicate darker, greener, bluer, or duller variations.

The principal shortcoming with color management software is that the software does not provide data between different vendor fabric color submissions. In other words, while the software program can predict whether a given batch is within tolerance, it cannot differentiate between differing batches that are within the tolerance range. For instance, assume two color samples are analyzed using color management software and are found to be within the tolerance limits. However, sample A has a large positive deviation and sample B has a large negative deviation. While each sample has an acceptable statistical deviation from the center point, the deviation between the two samples is inordinately large. Visually, sample A and sample B appear to be drastically different hues of the same color. As a result, the color management software fails to correlate with the visual differences between samples.

Of course, a designer can use historically accepted batches based on a color standard to determine whether accepted batches have a positive or negative deviation. However, this method requires a large pool of color samples that have been accepted and/or rejected. To obtain this data, a designer must go through the costly, time-consuming process of gathering numerous samples from numerous vendors, inspecting each sample, and comparing it to the proposed color standard. This process is highly inefficient and time consuming, which can lead to increased costs, wasted resources, and reduced profits.

Therefore, what is needed is a color management process that eliminates the inefficiencies described above by providing a directed color standard which better correlates to the visual differences between otherwise acceptable color samples before a designer receive a large number of sample submissions.

SUMMARY OF THE INVENTION

The present invention is directed to a process of creating a directed color standard. In essence, a designer provides a fabric with a proposed color. The designer then measures the color using any well known measuring technique and establishes a color standard. Then, the designer measures the provided fabric at various other locations. Because of the inherent variability of both the dye and the fabric, different measurements will be obtained. Finally, this data is used to create an acceptable directed color tolerance. Advantageously, this process allows a designer to produce a color standard that more accurately reflects the desired final product.

In addition, the present invention discloses a method of utilizing the directed color standard to effectively manage color. First, a directed color standard is created in accordance with the present invention. Next, the color standard is communicated to a vendor, which produces a product utilizing the directed color standard. Then, the product is delivered to the designer. The designer can accept or reject the product based on a comparison of the delivered product to the directed color standard. Advantageously, this process allows a designer to reduce the number of rejected color samples from various vendors, reducing costs and improving the efficiency of the process to all interested parties.

In accordance with the foregoing, it is an object of the invention to create a process for creating a directed color standard.

Still another object of the current invention is to provide a method of utilizing a directed color standard to effectively manage color.

Yet another object of the present invention is to utilize a directed color standard to improve the efficiency of a color matching process.

Still another object of the present invention is to utilize a color management method in conjunction with a directed color standard to reduce the costs of a color management system.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

FIG. 2A is a schematic diagram of a process for managing color utilizing a directed color standard.

DETAILED DESCRIPTION OF THE PREFERRED EMBODIMENT

A detailed illustrative embodiment of the present invention is disclosed herein. However, techniques, systems and operating structures in accordance with the present invention may be embodied in a wide variety of forms and modes, some of which may be quite different form those in the disclosed embodiment. Consequently, the specific structural and functional details disclosed herein are merely representative, yet in that regard, they are deemed to afford the best embodiment for purposes of disclosure and to provide a basis for the claims herein that define the scope of the present invention. The following presents a detailed description of a preferred embodiment of the present invention.

Initially, the use of the terms "designer" and "vendor" are not meant to limit the scope of the current invention. A designer, as used in the present application can be any individual or entity. For instance, by way of non-limiting examples, a designer can be an individual fashion designer, a dye house, a fabric mill, a retail outlet, a wholesale outlet, or some combination thereof.

In addition, the use of the terms "fabric," "garment," "product," and the like are not meant to limit the scope of the present invention. Rather, the terms are used interchangeably and are meant to be merely illustrative in nature of certain aspects of the present invention.

Moreover, well known methods, procedures, and substances for both carrying out the objectives of the present invention and illustrating the preferred embodiment are incorporated herein but have not been described in detail as not to unnecessarily obscure aspects of the present invention.

Figure 1:
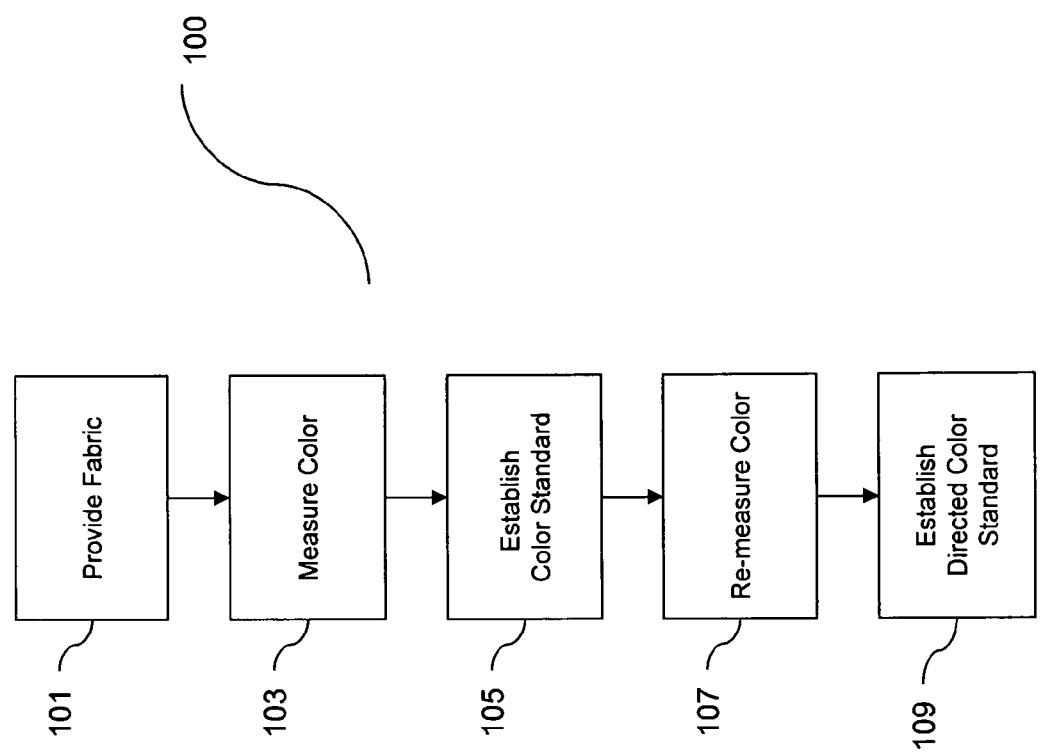
FIG. 1 is a schematic diagram depicting a process for creating a directed color standard.

Referring now to FIG. 1, depicted is a method of creating a directed color standard 100. Initially, fabric is provided 101. The fabric can be of any quality and constructed from any type of material. In addition, the fabric can come from any entity. Typical entities include dye houses, in-house research and development, retail outlets, wholesale outlets, fabric mills, and sew shops. Non-limiting examples of fabrics include fabrics comprised of natural fibers, fabrics comprised of synthetic fibers, and combinations of the two.

The fabric must have some color. As used herein, the term color is intended to encompass any perceivable color by the human eye in the visible spectrum. In addition, any reference to a specific color, e.g., blue, is merely exemplary and not intended to limit the scope of the invention. Providing specific colors on fabrics is well known in the art. For example, a fabric can be dyed with a jet machine as is well known in the art. Preferably, the fabric is conditioned in a well known manner. Of course, any other method of providing color on a fabric can be used without departing from the spirit of the invention.

After obtaining an acceptable fabric sample, a color is measured 103. Any method of measuring a color is acceptable, including visual inspection, visual inspection within a light box, and electronic determination. Preferably, the color standard uses an electronic determination means. In the preferred embodiment, the electronic means comprises reflectance data determined by a spectrophotometer. Of course, any other electronic means, well known in the art, can be used without departing from the spirit of the invention.

Next, the color measurements are used to determine a color standard 105. Preferably, the spectrophotometric reflectance data is entered into a software program to produce an initial color standard. For instance, MATCHWIZARD™ PRO color matching software, available from Clariant Corporation of Charlotte, N.C., USA and ColorTools® software from DataColor Corporation of Lawrenceville, N.J., USA are well known in the art. Advantageously, this initial color standard can be stored in a database for accurate record maintenance and fluid communication of the standard to a separate entity. Any other well known method of establishing a color standard is acceptable.

After establishing color standard 105, the provided fabric is re-measured at differing points of the fabric 107. Again, any method of determining color is acceptable, including visual inspection, visual inspection within a light box, and electronic determination. Preferably, the color standard uses an electronic determination means. In the preferred embodiment, the electronic means comprises reflectance data determined by a spectrophotometer. Of course, any other electronic means, well known in the art, can be used without departing from the spirit of the invention.

Because the provided fabric has inherent deviation within itself, the measurements taken at this step will likely be different than the original measurement.

The second series of measurements is used to establish a second, directed color standard 109. In a preferred embodiment, the second series of reflectance measurements are entered into a well known software program as previously described. This second series of color measurements can be used to create a separate color standard and stored on a database. The second, directed color standard has either a positive or negative deviation from the initial color standard. Comparing the two color standards allows any entity to determine the positive or negative deviation from the initial color standard, providing direction as to the inherent positive or negative deviation of the source fabric.

Alternatively, the initial color standard can be modified by shifting the center point of the color standard curve towards the positive or negative deviation while lowering the allowable tolerance level. This results in a directed color standard. Preferably, the directed color standard can be stored in a database for accurate record maintenance and fluid communication of the standard to a separate entity. Of course, any other method of storing a directed color standard can be used without departing from the spirit of the invention.

Figure 3:
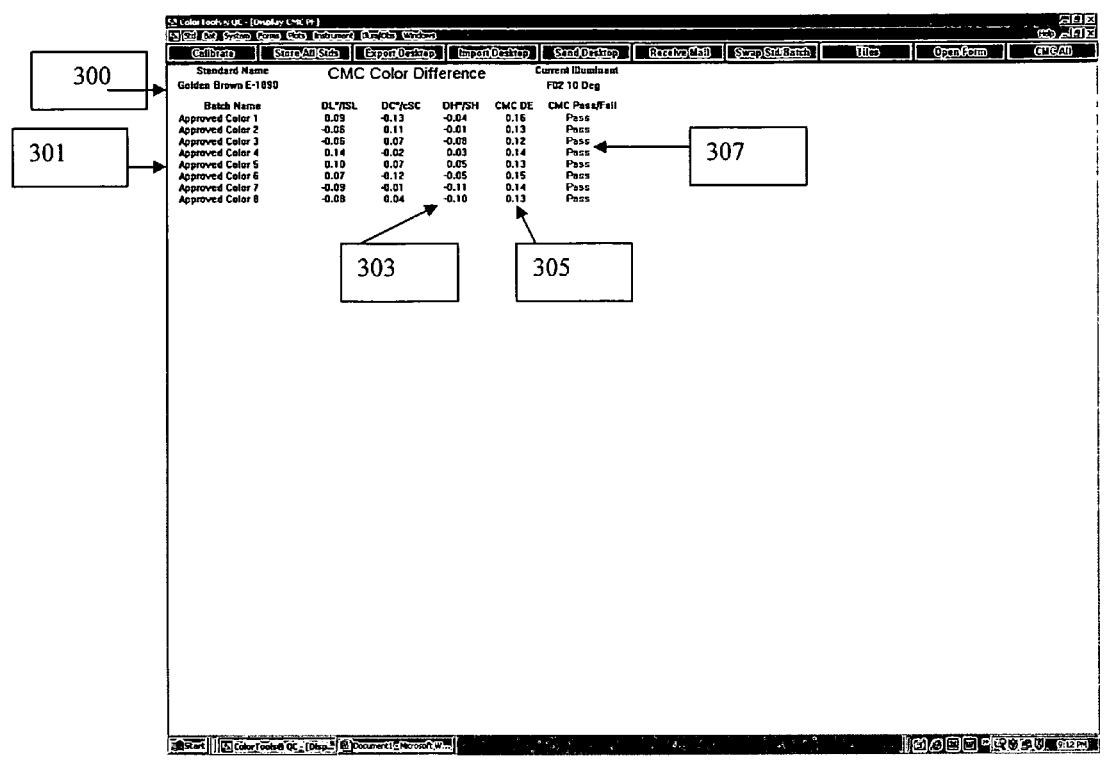
FIG. 3 is a screenshot of the resulting measurements used in creating a directed color standard.

FIG. 3 depicts the resulting data used to create a directed color standard. Data points 301 are stored in a database and comprise hue difference data 303, total deviation data 305, and quality control data 307. In this example, data points 301 are obtained from measuring a provided piece of fabric at various different points with a spectrophotometer. As can be seen by deviation data 305, the fabric has an inherent variability from initial color standard 300, which accounts for hue difference data 303. Quality control data 307 is a depiction of whether deviation data 305 is within acceptable tolerance limits. These limits can be set to any level as is well known in the art. Preferably, the tolerance is less than 1.00.

As FIG. 3 illustrates, the inherent color variability of the provided fabric correlates in one direction. In this example the correlation is negative. As a result, data points 301 can be used to create a negatively directed color standard. For instance, any of data points 301 can be stored on a database as a second color standard. When an entity compares initial color standard 300 to the directed color standard, it is directed to provide a fabric sample that negatively correlates with the initial color standard.

Of course, one skilled in the art will realize that data points 301 can be combined in any manner to create a directed color standard. For instance, a simple average, weighted average, or any other well known statistical method can be used to create a directed color standard from data points 301 without departing from the spirit or scope of the invention.

Figure 2B:
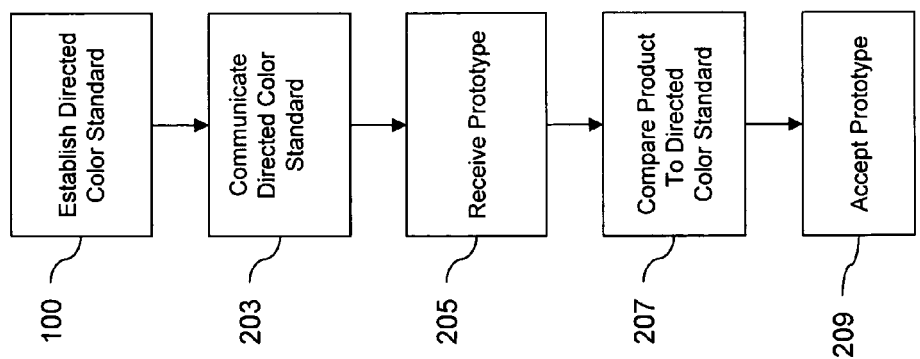
FIG. 2B is a schematic diagram of a process for accepting a conforming color product utilizing a directed color standard.
Figure 2C:
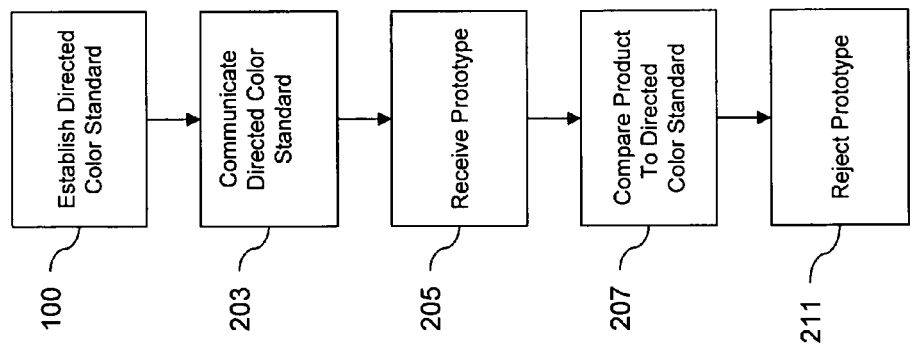
FIG. 2C is a schematic diagram of a process for rejecting a non-conforming color product utilizing a directed color standard.

A directed color standard allows a designer to more efficiently manage color deviations associated with differing batches of colored fabric. FIGS. 2A-2C depict such a process.

The first step in the color management process is to establish a directed color standard 100 as previously described. Directed color standard 100 is then communicated to an entity 203. The directed color standard can be communicated by any well known means, including mail delivery, express mail delivery, or electronic delivery. Preferably, the directed color standard is sent electronically to an entity. In addition, the directed color standard may be sent to a plurality of entities.

It is also contemplated that other information can be communicated to an entity as well. For instance, data related to a dye formula, information related to a specific type of fabric to be utilized, or any other well known data related to the desired utilization of the directed color standard can be communicated.

The entity receiving the color standard and/or other information related to the directed color standard utilizes it to create a product. The product can be any type of product, including a roll of fabric, a garment, a dye composition, or any other well known product capable of utilizing a directed color standard.

After the entity produces the product according to the directed color standard, the designer receives a sample of the product 205 from the entity. A designer can receive the product in any way. Non limiting examples include including mail delivery, express mail delivery, or electronic delivery. Preferably, a physical sample of the product is received by the designer.

The designer then proceeds to compare the product received with the directed color standard 207. The comparison can be made by any well known means, including visual inspection, visual inspection within a light box, and electronic determination. Preferably, the color standard uses an electronic determination means. In a preferred embodiment, the electronic means comprises reflectance data determined by a spectrophotometer. Of course, any other electronic means, well known in the art, can be used without departing from the spirit of the invention. In a more preferred embodiment, the comparison is made by both visual inspection and a spectrophotometer. This provides a designer with an additional layer of quality control.

After comparing the sample to the directed color standard, a designer can accept the sample 209 as shown in FIG. 2B or reject the sample 211 as shown in FIG. 2C. If a designer accepts the sample, it can place an order for a batch. If the designer rejects the sample, it can ask for another sample from a different batch or refuse to order from that entity. Of course, the designer can perform any additional step after accepting or rejecting the sample, all of which are well known in the art.

Figure 4:
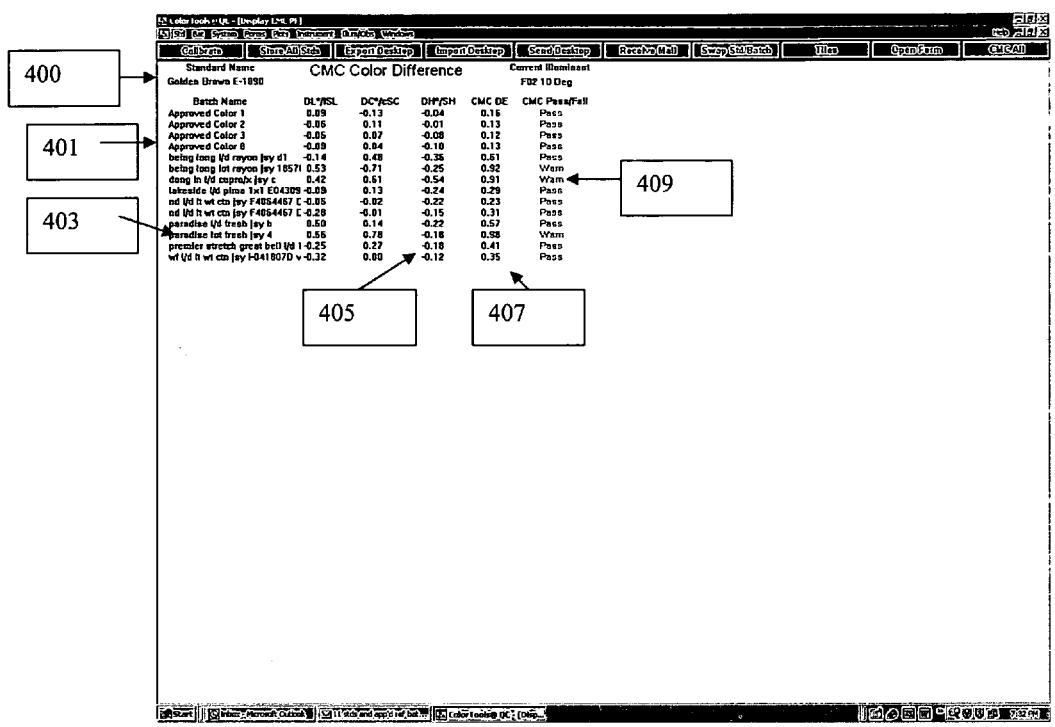
FIG. 4 is a screenshot depicting the improved batch acceptance of samples submitted for the first time utilizing a directed color standard.

Referring now to FIG. 4, depicted is the improved frequency of accepted initial color sample submissions in accordance with the present invention. Initial color standard 400, directed color standards 401 and initial color submission data 403 are stored in a database and comprise hue difference data 405, total deviation data 407, and quality control data 409. In this example, multiple directed color standards 401 are determined in accordance with the disclosure above. As can be seen by deviation data 407, initial color submission data 403 contains a deviation from initial color standard 400, which accounts for hue difference data 405. Quality control data 409 is a depiction of whether deviation data 407 is within acceptable tolerance limits. These limits can be set to any level as is well known in the art. Preferably, the tolerance is less than 1.00.

As can be seen in FIG. 4, directed color standards 401 have negative correlation to initial color standard 400 as depicted by hue difference data 405. By comparing directed color standards 401 to initial color standard 400 entities submitted color standards that also were negatively correlated with initial color standard 400, as depicted by initial color submission data 403. Importantly, in this example, the initial color submissions will be accepted because both the deviation from initial color standard 400 is within acceptable limits (as depicted by quality control data 409) and the initial color submissions are correlated to the directed color standard (as depicted by hue difference data 405). As a result, an entity submitting initial color data 403 will be approved on an initial submission, resulting in improved efficiency and lowered costs for both the submitting entity and the designer.

What is claimed is:

1. A method for managing color comprising the steps of:
   establishing a directed color standard;
      wherein said directed color standard is established by providing a fabric with a color;
      measuring color reflectance data of said color a first time;
      establishing a color standard for said color using said color reflectance data of said color;
      measuring color reflectance data of said fabric a second time; and
      establishing a directed color standard using said color reflectance data of said fabric;
   communicating said directed color standard to an entity;
   receiving at least one product from said entity, wherein said product is produced using said directed color standard; and
   comparing said product to said directed color standard.

2. The method of claim 1 further comprising the step of accepting said product after comparing said product to said directed color standard.

3. The method of claim 1 further comprising the step of rejecting said product after comparing said product to said directed color standard.

4. The method of claim 1 wherein said product is selected from the group consisting of natural fabric, synthetic fabric, or a combination thereof.

5. The method of claim 1 wherein said entity is selected from the group consisting of a dye house, a fabric mill, or a combination thereof.

6. The method of claim 1 wherein comparing said product to said directed color standard is selected from the group consisting of visual inspection, digital inspection, spectrophotometric inspection, or a combination of visual inspection and spectrophotometric inspection.

7. The method according to claim 1 wherein color reflectance data is measured using a Spectrophotometer.

8. The method according to claim 1 wherein said step of establishing a color standard is accomplished by a software program.

9. The method according to claim 1 wherein said step of establishing a directed color standard is accomplished by a software program.

10. The method of claim 1 wherein said directed color standard is stored in a database.

11. The method of claim 1 wherein the step of communicating said directed standard is selected from the group consisting of: electronic communication, posting on a website, or physical delivery.

12. The method of claim 1 wherein said directed color standard is derived using a weighted average.

* * * * *